United States Patent [19]

Dewey et al.

[11] Patent Number: 5,648,597
[45] Date of Patent: Jul. 15, 1997

[54] ALPHA-1-ACID GLYCOPROTEIN TRANSGENIC MICE

[75] Inventors: Michael J. Dewey, Columbia, S.C.; Heinz Baumann, Buffalo, N.Y.

[73] Assignees: University of South Carolina, Columbia, S.C.; Health Research, Inc., Buffalo, N.Y.

[21] Appl. No.: 511,470

[22] Filed: Apr. 20, 1990

[51] Int. Cl.$^6$ .............................. C12N 5/00; C12N 15/00
[52] U.S. Cl. .............................. 800/2; 800/DIG. 1; 935/60
[58] Field of Search .............................. 800/2, DIG. 1–5; 935/60

[56] References Cited

PUBLICATIONS

Cooper et al., Nucleotide Sequence of the Mouse $\alpha_1$–Acid Glycoprotein Gene 1, Biochemistry (1987) vol. 26 pp. 5244–5250.

Dente et al., Expression of human $\alpha$1–acid glycoprotein genes in cultured cells and transgenic mice, J. Biological Chemistry, (1985) vol. 260, No. 7, pp. 259–266.

Reinke et al., Rat $\alpha_1$–Acid Glycoprotein, J. Biological Chemistry, (1985) vol. 260 No. 7., pp. 4397–4403.

Ricca et al., Nucleotide Sequence of Rat $\alpha_1$–Acid Glycoprotein Messenger RNA J. Biological Chemistry, vol. 256, No. 21, pp. 11199–11202.

Tomei et al., Use of transgenic mice for the characterization of human alpha 1–acid glycoprotein (orosomucoid) variants, Hum. Genet. (1989) 84:89–91.

Dente, L. et al. (1988) "Expression of Human $\alpha$1–Acid Glycoprotein Genes in Cultured Cells & in Transgenic Mice". Genes & Development 2:259–266.

Van Brunt, J. (1988) "Molecular Farming: Transgenic Animals as Bioreactors" Biotechnology 6:1149–1154.

*Primary Examiner*—Deborah Crouch
*Attorney, Agent, or Firm*—Brumbaugh, Graves, Donohue & Raymond

[57] ABSTRACT

The mice of this invention heritably carry alpha-1-acid glycoprotein (AGP) genes which may be introduced by the transgenic methodology. These animal models are useful for various purposes including 1) assessment of the in vivo role of AGP in the clearance of individual drugs; 2) assessment of the influence of AGP on the pharmacological activity of individual drugs; 3) testing of hypotheses concerning the function of AGP; and 4) identification of the AGP gene cis-acting regulatory features.

2 Claims, 4 Drawing Sheets

ALPHA-1-ACID GLYCOPROTEIN TRANSGENIC MICE

BACKGROUND OF THE INVENTION

The mammals of this invention heritably carry alpha-1-acid glycoprotein (AGP) genes which may be introduced by the transgenic methodology. These animal models are useful for various purposes including 1) assessment of the in vivo role of AGP in the clearance of individual drugs; 2) assessment of the influence of AGP on the pharmacological activity of individual drugs; 3) testing of hypotheses concerning the function of AGP; and 4) identification of the AGP gene cis-acting regulatory features.

AGP, a human plasma glycoprotein produced by the liver, is an acute-phase reactant—i.e., its concentration in the blood increases following inflammation.

AGP and serum albumin, the most important drug binding proteins in the plasma, present complimentary binding specificities. AGP binds mainly basic and neutral drugs whereas albumin is largely responsible for the plasma binding of acidic drugs. Such plasma binding of drugs by AGP is likely to be accompanied by important pharmacokinetic consequences (see Kremer et al., *Pharmacological Review* 40:1–47 (1988)). Much literature documents the in vitro binding of specific drugs by AGP whereas few studies attempt to measure the in vivo physiological and pharmacological effects of such binding. The determination of these effects is specifically addressed by the invention.

SUMMARY OF THE INVENTION

An important aspect of the invention provides a series of transgenic animals, transgenic for rat alpha-1-acid glycoprotein, that contain basal, i.e., non-acute phase, serum levels of AGP far in excess of that normally found. The genetic trait responsible for these high levels is heritable and imparts a uniformly high level of AGP to all animals that carry it. Comparison of the response of these animals to specific drugs with that of control animals will provide important in vivo information as to the specific role of AGP in the clearance, tissue distribution, and action of individual drugs.

The normal function of AGP is a matter of speculation. From in vitro studies, AGP is suscepted to influence immunefunction (Chui et al. *Immunology* 32:997–1005 (1977)), coagulation (Beckett et al. *Nature* 181:711-712-712 (1958)), phagocytosis (Oss et al. *Immunol. Commun.* 3:321–328 (1974)), graft rejection (Mowbray *Transplantation* 1:15–20 (1963)), and wound healing (Boeg-Hansen *Proc Fourth Lectin Meeting* (1981)). The invention provides animal models to study the function of AGP and to test in vivo whether any of the above-suggested actions of AGP have any relevance to the whole animal.

Another application of the invention relates to the regulation of AGP, especially as a tool to discover those cis-acting elements that impart particular components to the AGP expression profile. The regulation of AGP is a complex process with regard various aspects of its expression profile—time, level, tissue-specificity, and inducibility (Baumann *In Vitro Cellular and Developmental Biology* 25:115 (1989)). In the decidual cells of the pregnant rat uterus, there is a burst of AGP synthesis 1–5 days post-implantation; by parturition, the level of uterine AGP synthesis declines to near zero. AGP is expressed at high levels in the liver and is secreted into the blood stream where it is one of the more abundant proteins. AGP is also expressed on the surface of leukocytes, including resting T and B cells.

AGP synthesis also increases several fold during an acute phase response (Baumann, H. et al. *J. Biol. Chem.* 256:10145–10155 (1981); Ricca, G. A. et al. *J. Biol. Chem.* 256:11199–11202 (1981); Koj, A. et al. *Biochem J.* 206:545–553 (1982); Koj, A. et al. Biochem J. 224:505–514 (1984)). The major acute phase inducers of AGP synthesis are the cytokines interleukin-1 (IL-1) and interleukin-6 (IL-6), which act additively to induce transcription of the AGP gene. In addition to these peptide factors, glucocorticoids stimulate AGP expression in rats and mice (Baumann, H. et al., *J. Biol. Chem.* 256:10145–10155 (1981); Baumann, H. et al., *J. Biol. Chem.* 258:563–570 (1983); Vannice, J. L. et al., *DNA* 2:205–212 (1983); Reinke, R. et al., *J. Biol. Chem.* 260:4397–4403 (1985)) and act in synergy with IL-1 and IL-6 during acute inflammation. Baumann, H. et al. *Am. NY Acad Sci* 557:280 1987; Andus, T. et al., *Eur. J. Immunol.* 18:739–746 (1988).

Transfection experiments with hepatic cell lines have demonstrated that separate elements within the 5'-flanking region of the rat AGP gene are responsible for induction by steroid hormones and by inflammatory cytokines. Baumann, H. et al., *Molec. Cell. Biol.* 6:2551–2561 (1986); Prowse, K. R. et al., *Molec. Cell. Biol.* 8:42–51 (1988). Glucocorticoid regulation is localized to a region between nucleotides −120 and −64 relative to the transcriptional start site. Sequence analysis of this region has revealed a glucocorticoid regulatory element (GRE) similar to that described for other genes such as the metallothionein gene and mouse mammary tumor virus (Karin, M. et al., *Nature*, 308:513–519 (1984); Baumann H. et al., *Molec. Cell. Biol.* 6:2551–2561 (1986); Reinke et al., supra; Klein, E. S. et al., *Molecular Endocrinology* 2:1343–1351 (1988). Another regulatory sequence, termed the distal regulatory element (DRE), imparts inducibility by inflammatory cytokines. The DRE is located between positions −5300 and −5150 relative to the transcriptional start-site and functions in either orientation.

DESCRIPTION OF THE FIGURES

FIG. 2 is a Southern blot analysis of HindIII-digested tail. DNAs from transgenic mice 9.5-1, 9.5-2, 9.5-3 and 10.7-2. The blots were hybridized to cDNA plasmid pIRL10 DNA, which corresponds to the full-length rat AGP mRNA and hybridizes to rat (R) and mouse (M) DNAs. For each line, the founder mouse (left) and one of its transgenic offspring (right) are shown. The breeding data indicated that the founder for line AGP 9.5-2 was mosaic, explaining the lower band intensities for this mouse as compared to that from its transgenic offspring. The HindIII fragment within the AGP coding sequence (labelled I in the figure), the novel HindIII junction fragment generated by head-to-tail concatenation of the gene (labelled J), and another major (multicopy) fragment (labelled A) resulting from rearrangement during integration are indicated.

DETAILED DESCRIPTION OF THE INVENTION

Alpha-1-acid glycoprotein (AGP), is produced in the mammalian liver and secreted into the bloodstream. AGP expression is regulated by steroid hormones and by mediators of the acute phase response. Transgenic mice containing rat AGP gene constructs with and without the DRE have been produced and characterized.

Five transgenic lines were produced from a 9.5 kb genomic AGP construct containing 4.7 kb of the 5' flanking region but lacking the DRE. Another transgenic line was derived from a 10.7 kb clone that contains 5.3 kb of 5' flanking sequences including the DRE. The two different gene constructs and five transgenic lines provided by this invention yield a broader spectrum of results from experiments conducted on any one of these animals lines.

These animal models provide a means of exploring 1) the in vivo role of AGP in the clearance of individual drugs; 2) the influence of AGP on the pharmacological activity of individual drugs; 3) the function of AGP, and 4) cis-acting regulatory features that determine the AGP expression profile. All transgenic mice produced high levels of immunologically detectable rat AGP in the circulation, comparable to or in excess of that found in normal rats. There were correspondingly high concentrations of rat AGP transcripts in the liver. Transgene expression in all lines was induced in response to dexamethasone and during an acute inflammation resulting from liposaccharide (LPS) treatment. The DRE-containing transgene underwent a greater induction in response to LPS than to dexamethasone; the transgene lacking the DRE responded similarly to both treatments. In cultured primary hepoatocytes, the DRE-containing transgene was induced by the acute phase cytokines IL-1 and IL-6, and by dexamethasone, administered individually or in combination; the transgene lacking the DRE responded only to dexamethasone, and was not affected by the peptide hormones.

These results provide in vivo evidence that a minimum of two upstream sequences are responsible for the inflammatory induction of rat AGP. One element, which is located within the smaller 9.7 kb restriction fragment, is responsive to glucocorticoids and is apparently the GRE located close to the transcriptional start site. The other element, the DRE, is located much further upstream and is responsible for imparting responsiveness to the acute phase cytokines.

Production of Transgenic Mice Carrying Rat AGP Genes

Figure 1:
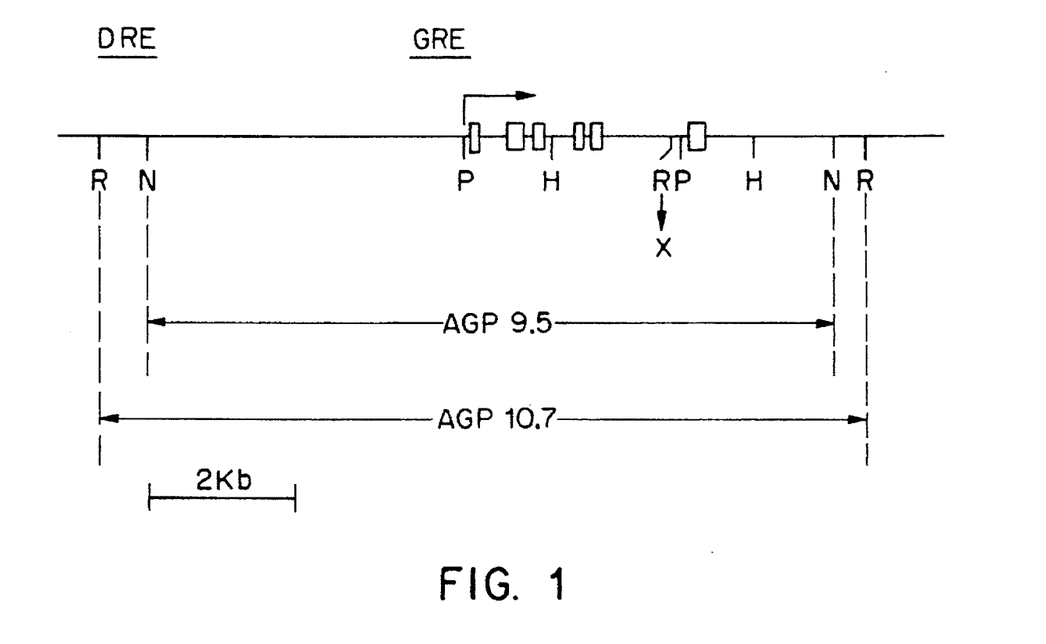
FIG. 1 is a restriction map of the rat AGP gene. Solid blocks indicate the six exons of AGP and the upper arrow the transcription start-site. Two regulatory regions, the GRE (glucocorticoid regulatory element—AGP 9.5) and the DRE (distal regulatory element—10.7), are shown. The restriction endonuclease sites are: HindIII (H), NdeI (N), PstI (P), and EcoRI (R).
Figure 2:
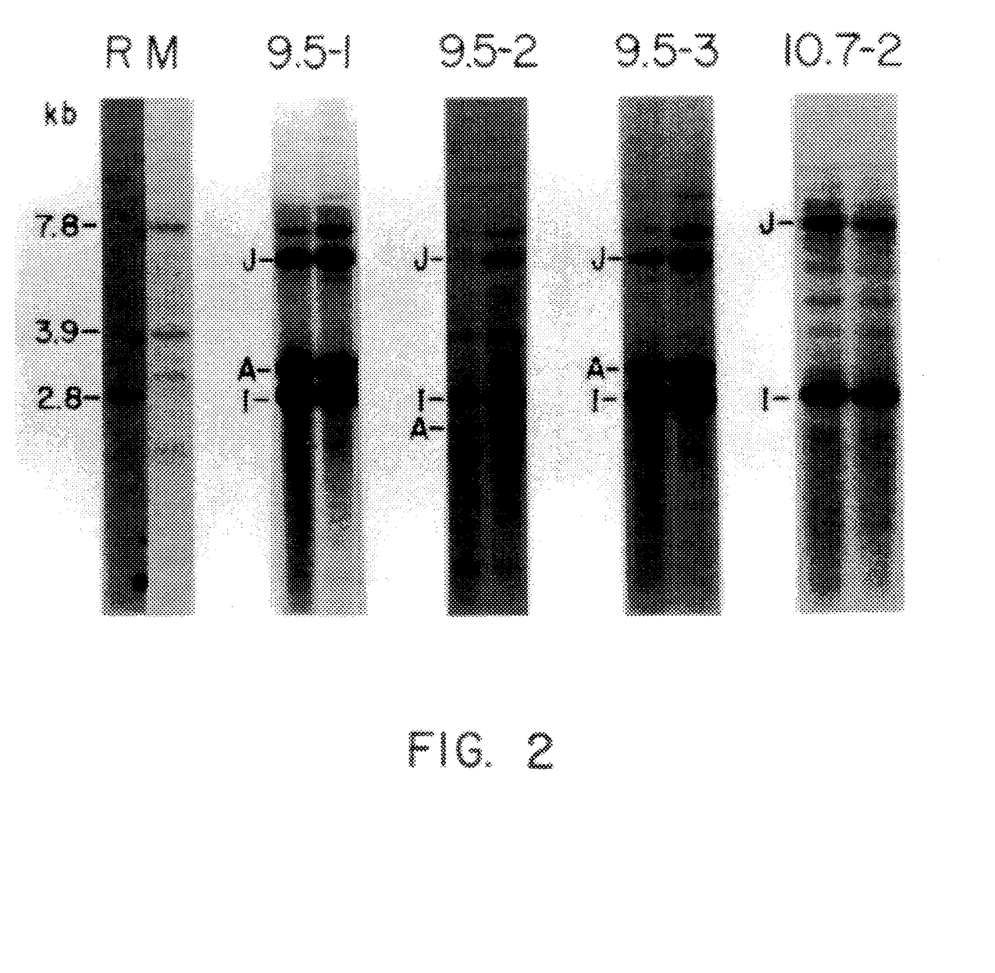

Two rat AGP gene constructs as shown by FIG. 1 were prepared. Plasmid pAGP 9.5 contains a 9.5 kb genomic segment which encompasses the entire coding sequence along with 4.7 kb of the 5' flanking region and 1.6 kb of the 3' flanking region; the GRE, but not the DRE, is present within this DNA segment. Plasmid pAGP 10.7 contains an additional 600 bp of DNA at both the 5' and 3' ends (FIG. 1), and includes the cytokine-responsive DRE as well as the GRE. The AGP 9.5 transgenic lines were generated by microinjection of the 9.5 kb NdeI fragment. The AGP 10.7-2 line was generated by microinjection of the 10.7 kb EcoRI fragment.

Restriction fragments for microinjections were subcloned fragments of an AGP genomic clone that was previously isolated from a library of Sprague-Dawley rat DNA in Charon 4A (FIG. 1). Plasid pAGP 9.5 was constructed by subcloning the NdeI fragment that spans the region between −4700 and +4800 into pUC13. Plasmid pAGP 10-7 was generated by converting the KpnI site at +5400 into an EcoRI site and abolishing the EcoRI site in the fifth intron by blunt-end ligation. The resulting EcoRI fragment, which spans the region between −5300 to +5400, was subcloned into pUC13.

A solution containing 2 μg/ml DNA was microinjected into the male pronuclei of (C57BL/6×DBA/2)F$_2$ embryos using procedures described by (Hogan, B. L. M. et al., *Manipulation of the Mouse Embryo: A Laboratory Manual* (1986)). Injected embryos were implanted into the uteri of pseudopregnant foster females and allowed to develop to term. Transgenic animals were identified by Southern analysis of tail DNA or by immunoelectrophoresis of plasma, as described below.

Dexamethasone treatment was by two 50 μg intraperitoneal injections of the hormone suspended in 0.1 ml phosphate-buffered saline 24 and 16 h before the animals were sacrificed. Acute inflammation was elicited by a single 50 μg injection of *Escherichia coli* lipopolysaccharide (serotype 0127:B8; Sigma) in 0.1 ml phosphate-buffered saline 24 h prior to sacrifice.

A total of nine founders were identified among the animals derived from microinjected embryos. Five of these were from the 9.5 kb genomic AGP clone and four from the larger 10.7 kb clone. As the data from Table 1 shows, all five of the AGP 9.5 derived founders transmitted the respective transgenes to their offspring.

TABLE 1

| Germ Line Transmission of Rat AGP Transgenes | | |
| --- | --- | --- |
| Founder | Sex | Transmission Frequency* |
| AGP 9.5-1 | female | 14/31 |
| AGP 9.5-2 | female | 5/45 |
| AGP 9.5-3 | female | 6/14 |
| AGP 9.5-4 | female | 9/26 |
| AGP 9.5-5 | male | 12/60 |
| AGP 10.7-1 | male | 0/6 |
| AGP 10.7-2 | male | 21/30 |
| AGP-10.7-3 | female | 0/20 |
| AGP 10.7-4 | female | 0/36 |

*Number of progeny with transgene/total.

Two of the founders, AGP 9.5-2 and AGP 9.5-5, transmitted to substantially fewer than 50% of their offspring, and are presumed to be mosaic as a result of transgens incorporation some time after the first cleavage of the injected embryos. See Wilkie, T. M. et al., *Develop. Biol.* 118:9–18 (1986).

Only one of the four AGP 10.7 derived founders (AGP 10.7-2) transmitted to its offspring. AGP 10.7-1 sired only six offspring before it died; AGP 10.7-3 and AGP 10.7-4 failed to transmit the transgens to 20 and 26 offspring, respectively.

Total DNA and RNA were isolated from whole tissues and analyzed by standard methods (Tseng-Crank, J. et al., *Genetics* 116:593–599 (1987)). For Northern (RNA) blot analysis, 15 µg of RNA were fractionated on 1.5% agarose gels containing 2.2M formaldehyde and transferred to nylon membranes. For Southern blotting, 10 µg of DNA were digested with HindIII, fractionated on 1.0% agarose gels, and blotted onto nylon membranes. Blots were hybridized to nick-translated pIRL-10 DNA, which contains a 850 bp insert corresponding to rat AGO mRNA (Baumann and Berger *Mol. Genet.* 201:525 (1985)). To distinguish rat-specific from mouse-specific AGP transcripts, end-labeled oligonucleotide probes were used. The mouse-specific probe was a 20 bp oligomer (5'CTCCGGGGTGATATCTGGCC 3') complementary to the mouse mRNA between residues 478 and 497 (Cooper, R. et al., *J. Biol. Chem.* 261:1849–1853 (1986)). The rat-specific probe was an oligomer (5' GGGGGTAGAGTGGGCATGGG 3') complementary to the rat mRNA between residues 694 to 713 (Ricca, G. A. et al., *J. Biol. Chem.* 256:11199–11202 (1981). Hybridization conditions for each oligomer were determined by criteria outlined in (Wallace, R. B., et al., *Nucleic Acids Res.* 9:879–893 (1981).

Southern analyses of DNA from transgenic mice demonstrated that the transgenes had incorporated as multiple, intact copies arranged as tandem head-to-tail concatenates. For example, HindIII-digested DNA from lines AGP 9.5-2, -2, and -3 yielded major hybridizing fragments at 2.9 kb and 6.6 kb. The former is an internal fragment within the gene and is evident in genomic blots of rat genomic DNA; the latter is a novel junction fragment generated from the head-to-tail concatenation of the multiple copies. However, each of the lines also exhibited a major (i.e., multi-copy) fragment which was most likely the consequence of some sort of rearrangement during integration. In lines AGP 9.5-1 and -3, this fragment was about 3.5 kb in length, whereas in AGP 9.5-2 it was 2.5 kb in length. All or most of the transgene copies in line AGP 10.7 appeared intact insofar as Hind III digestion generated the internal 2.9kb fragment and the predicted 7.8 kb junction fragment.

Estimates of transgene copy-number were determined by comparing band intensities on the Southern blots, using the AGP gene in rat genomic DNA as the single-copy standard. Among the lines tested, the transgene copy-number varied between 1–2 for AGP 9.5-2 to about 50 for AGP 9.5-1.

Synthesis and Secretion of Rat AGP in Transgenic Mice

Blood was collected from the retroorbital sinus in heparinized microhematocrit tubes and whole cells were removed by centrifugation.

The levels of rat AGP in plasma from the transgenic mice were monitored by rocket immunoelectrophoresis using rabbit antiserum specific for rat AGP; antiserum against mouse AGP was also used to measure the level of the endogenous protein. The immunoelectrophoretic plates were prepared in two sections: the first section (i.e., that closer to the cathode) contained rabbit anti-rat AGP serum, while the second section (i.e. that closer to the anode) contained rabbit anti-mouse AGP serum. Anti-mouse AGP serum does exhibit some cross-reactivity with rat AGP.

Figure 3:
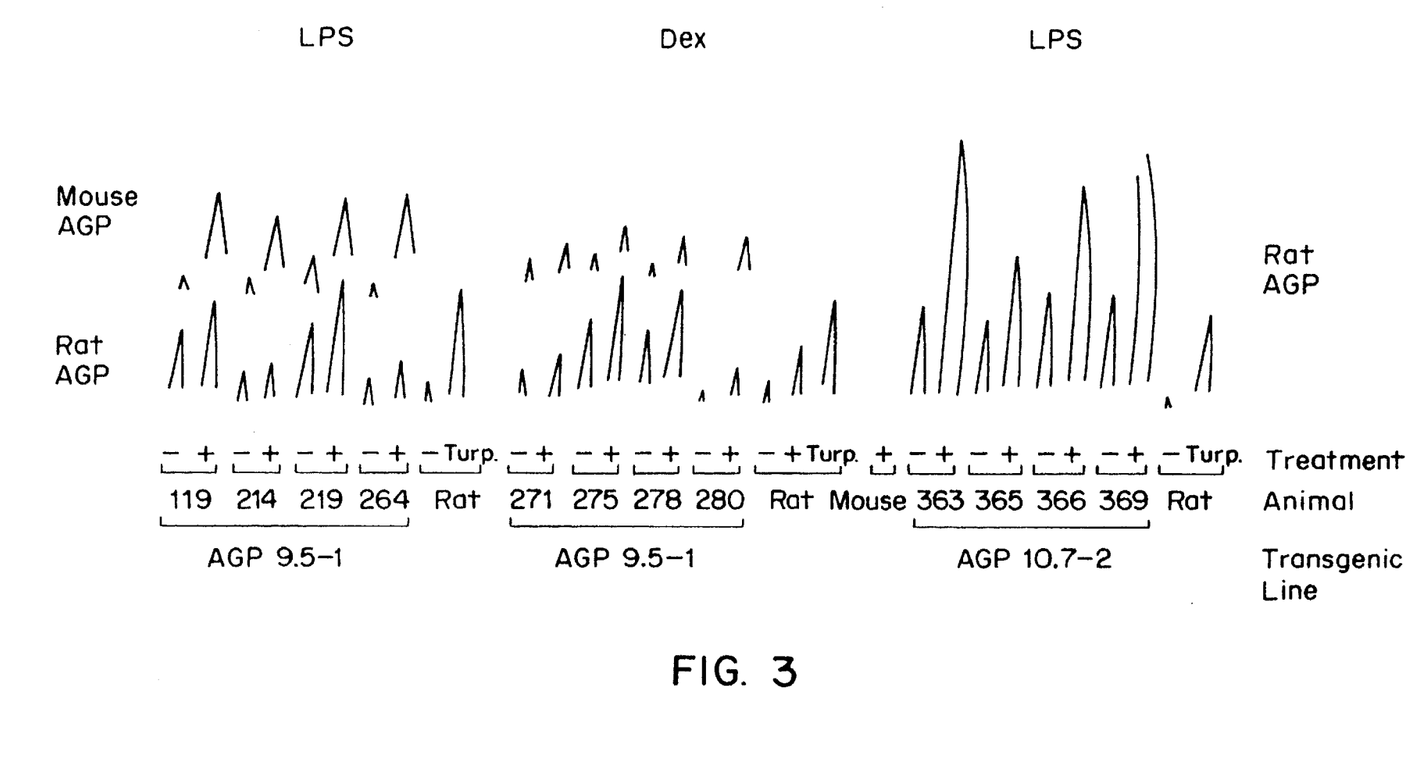
FIG. 3 is an immunoelectrophoretic analysis of AGP in the plasma of transgenic mice. Plasma samples from lines AGP 9.5-1 and AGP 10.7-2, either control (−) or induced (+) for 24 h with either bacterial lipopolysaccharide (LPS) or dexamethasone (Dex), were analyzed by immunoelectrophoresis using monospecific anti-rat AGP and anti-mouse AGP antibodies.

All nine transgenic founders and their respective progeny accumulate rat AGP in the blood serum in concentrations that are more abundant than that found in normal, non-inflamed rats and mice (See FIG. 3 and Table 2). Supranormal serum concentrations of AGP is an important attribute of these animal lines that render them useful for a number of studies which heretofore have been approachable only with the crudest of techniques.

TABLE 2

Transgene Expression Profiles

| AGP Line | Copy No. | Basal Level of Rat AGP mg/ml(S.D.) | Inducer | Fold Induction (S.D.) | Extra Hepatic Expression |
|---|---|---|---|---|---|
| 9.5-1 | 30–60 | 0.55(0.27) | LPS | 1.6(0.2) | n.d.* |
|  |  |  | Dex | 1.9(0.6) |  |
| 9.5-2 | 2–4 | 0.53(0.09) | LPS | 2.1(0.6) | Heart, Spleen |
| 9.5-3 | 10–20 | 1.1(0.28) | LPS | 2.5(0.8) | Heart, Spleen Submaxillary Gland, Brain |
| 9.5-5 | n.d.* | 4.5(0.82) | LPS | 1.2(0.1) | Heart, Spleen Submaxillary Gland |
| 10.7-2 | 10–20 | 2.2(0.83) | LPS | 3.9(1.0) | n.d.* |
|  |  |  | Dex | 1.9(0.4) |  |
| Rat | 1 | 0.26 | LPS | 5.5 |  |
|  |  |  | Dex | 2.5 |  |

*not determined.

There was considerable variation in the levels of rat AGP among the different transgenic lines. Line AGP 9.5-5 contained about 20-fold more protein than non-inflamed rats, or 2–3 fold the levels in inflamed (i.e., LPS treated) rats (Table 2). Other lines, such as AGP 9.5-1, -2, and -3, were intermediate between non-inflamed and LPS treated rats (Table 2) In spite of the apparent over expression of rat AGP in some lines, expression of endogenous mouse AGP appeared to be unaffected (not shown). Transgene copy number variation among the transgenic lines did not correlate with differences in expression levels (Table 2). Thus, rat AGP levels in transgenic lines AGP 9.5-1, -2, and -3 varied by two-fold, whereas transgene copy numbers varied by as much as 10- to 30-fold.

Plasma AGP concentrations were measured in response to LPS and dexamethasone. LPS induction in the AGP 9.5 transgenic lines was generally 1.2- to 2.5-fold (Table 2, FIG. 3). This contrasts with a 3.9-fold induction in line AGP 10.7-2, and a 5.4-fold induction in rats (Table 2, FIG. 3). Of interest is the finding that in the AGP 9.5 lines, LPS and dexamethasone induced transgene expression to about the same extents (i.e. 1.6-fold and 1.9-fold respectively), whereas in line AGP 10.7-2, LPS elicited a two-fold greater response than dexamethasone (i.e., 3.9-fold for LPS and 1.9-fold for dexamethasone). Levels of endogenous mouse AGP underwent a greater induction in response to LPS than in response to dexamethasone (FIG. 3); this is similar to what is observed in rats (Table 2). Thus, sequences present in the AGP 10.7-2 transgenic line, and absent from the AGP 9.5 lines, appears to be affecting the response of the transgene to LPS-mediated inflammation.

Tissue-Specific Expression of Rat AGP mRNA in Transgenic Mice

Figure 4:
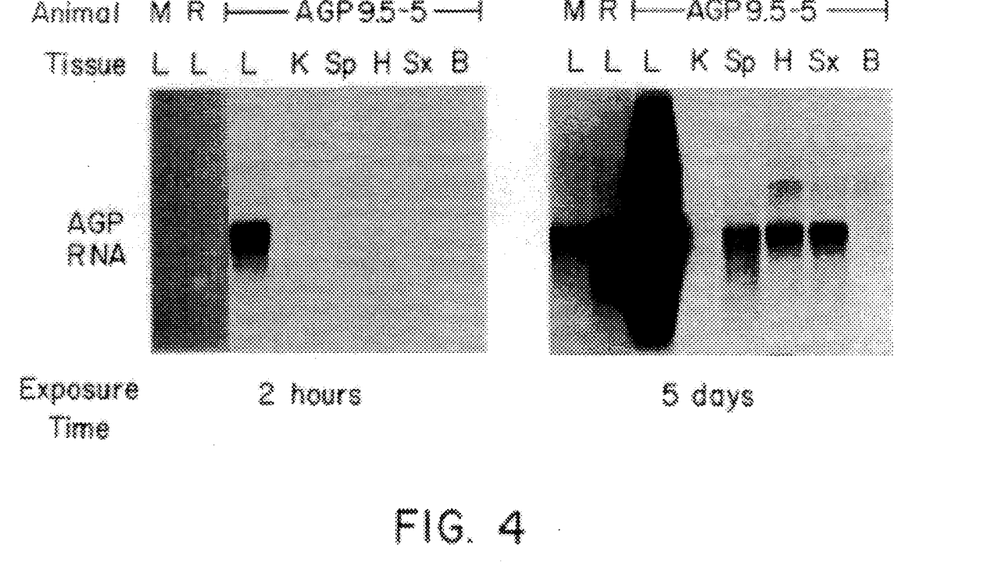
FIG. 4 illustrates the tissue-specificity of transgene expression in the AGP 9.5-1 liver. RNA from liver (L), kidney (K), spleen (Sp), heart (H), submaxillary gland (Sx), and brain (B) was subjected to Northern blot analysis using the rat cDNA plasmid pIRL-10 as probe. The blot was exposed for 2 hours and 5 days.

To measure AGP mRNA expression, total RNA was extracted from various tissues, blotted onto a nylon membrane, and hybridized to pIRL10, which is a rat cDNA probe that recognizes both the rat and mouse transcripts (Baumann and Berger, *Mol. Gen. Genet.* 201:505 (1985)). FIG. 4 shows the results of analysis of transgenic line AGP 9.5-5.

Liver is the major site of AGP mRNA production. Upon longer exposures of the autoradiograms, mRNA can be detected in spleen, heart, and submaxillary gland at levels some 100-fold less than in liver. Lines AGP 9.5-2 and AGP 9.5-3 exhibited similar patterns of mRNA expression, with some variation (Table 2). In all three lines, AGP mRNA was consistently observed in spleen and heart, though at higher levels in the latter (data not shown). Since the endogenous mouse AGP genes are not expressed to any appreciable extent anywhere but liver, we conclude that the transgene is functioning in extra-hepatic tissues. This is supported by the ability of a rat-specific, but not a mouse-specific, oligonucleotide probe to detect AGP mRNA in heart tissue from AGP 9.5-3 mice (unpublished observations).

Figure 5:
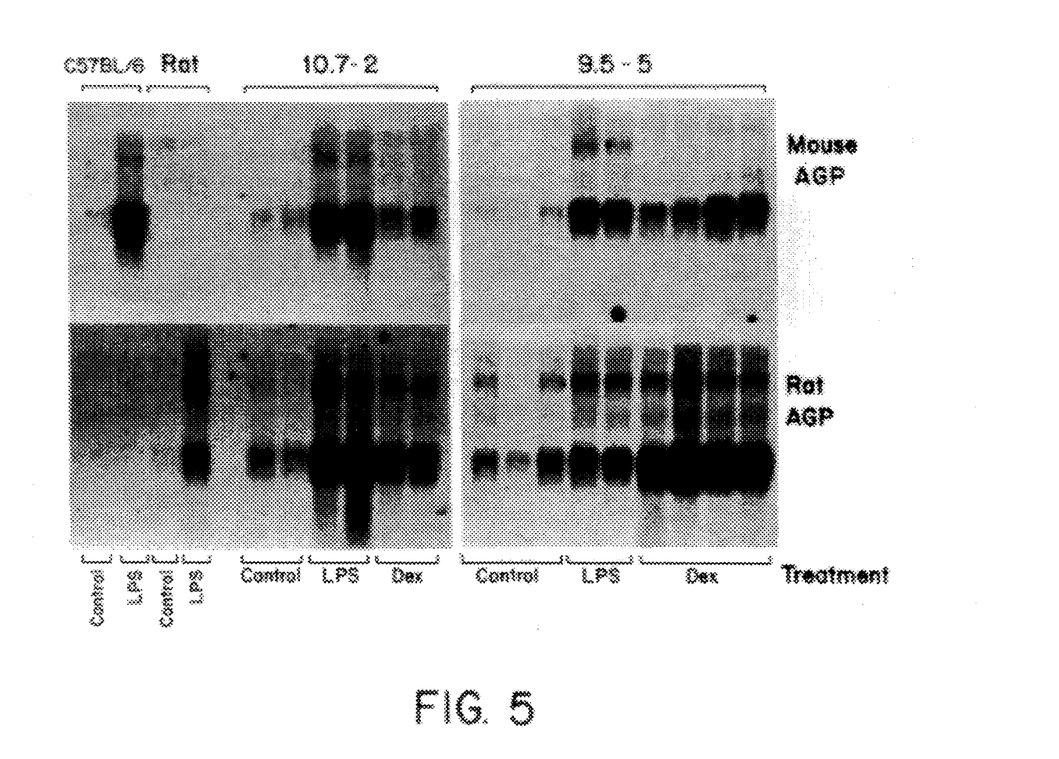
FIG. 5 illustrates liver-specific expression and induction of rat and mouse AGP mRNA. Total liver RNA was extracted from mice of transgenic lines AGP 9.5-5 and AGP 10.7-2, either uninduced (Control) or treated for 24 h with LPS or dexamethasone (Dex), and subjected to Northern blot analysis using a mouse-specific oligomer (top panel) or rat-specific oligomer (bottom panel).

To separately monitor mouse-specific and rat-specific mRNA expression, blots of liver RNA from each of the transgenic lines were hybridized to oligonucleotide probes specific for rat or mouse AGP transcripts. As FIG. 5 shows, an abundant RNA species hybridizes to the rat-specific AGP probe. This species comigrates with legitimate rat AGP mRNA, is absent from non-transgenic mice, and must therefore be derived from the rat AGP transgene. The concentrations of rat AGP mRNA in lines AGP 9.5-5 and AGP 10.7-2 are markedly greater than that in the control rats (FIG. 5) and correlate with the observed high levels of circulating AGP in these mice (Table 2). Thus, the high level of rat AGP in plasma is attributable in part to a correspondingly high concentration of mRNA in liver.

In response to either LPS or dexamethasone, the transgenic mice produced elevated levels of AGP mRNA (FIGS. 3 and 5, Table 2). However, fundamental differences in the induction profiles were observed between the AGP 9.5 lines and line AGP 10.7-2. In line AGP 9.5-5, the transgene underwent a large response to dexamethasone and a small, though significant, response to LPS; this is consistent with the presence of a steroid-sensitive element (i.e., the GRE) and the absence of a monokine-sensitive element (i.e., the DRE) in the 9.5 kb construct. A modest induction by LPS is not surprising, since the concentration of endogenous glucocorticoids is thought to increase secondarily in response to inflammatory cytokines during an acute phase (Besedovsky, H. et al., Science 233:652–654 (1983); Woloski, B. M. R. N. J. et al., Science 230:1035–1037 (1985)). In contrast to line AGP 9.5-5, the transgene in line AGP 10.7-2 underwent a greater response to LPS than to dexamethasone; this is what would be expected if both a DRE and a GRE are present and functioning within this construct.

These results indicate that rat AGP expression in transgenic mice carrying the shorter, 9.5 kb AGP gene is induced exclusively through its GRE. LPS acts indirectly through its effect on glucocorticoid levels. On the other hand, the larger 10.7 kb transgene, which contains the DRE (Prowse and Baumann 1988), does respond to LPS.

The following characteristics of transgene expression have been observed in non-inflamed AGP 9.5 transgenic lines:

1. The transgene was expressed in the liver at a level comparable to or in excess of that in uninduced rats.
2. In some non-hepatic tissues, transgene expression was detectable at low levels; heart and spleen were prominent among these.
3. Considerable variation in transgene expression was observed among lines; this did not correlate with transgene copy number, and must, therefore, be a consequence of different chromosomal environments at distinct integration sites.

Based upon these observations, it can be concluded that the major regulatory elements responsible for abundant expression of the AGP gene in liver, and for the relative silence of the gene in other tissues, is included within the 9.5 kb genomic fragment. The fact that transgene expression in the liver was the same or higher than that in normal rats also indicates that the sequences responsible for the characteristically high abundance of AGP are also present on this restriction fragment. Brinster et al. Proc. Natl Acad Sci 85:836 (1988)) reported that transgenes containing introns are transcribed more efficiently than genes lacking them, suggesting that regulatory sequences controlling a gene's expression level may not coincide with those controlling its tissue-specificity. Results reported herein with the 9.5 kb fragment would indicate that both types of regulatory sequences are present on that restriction fragment.

Previous in vitro transfection experiments using hepatoma cell lines implicated certain sequences upstream of the AGP structural locus as essential for the control of expression by steroid hormones and by inflammatory cytokines. The results presented herein provide an important confirmation of that work. Transgenic mice containing the 9.5 kb restriction fragment produced elevated levels of AGP after treatment with LPS, as did animals containing the 10.7 kb fragment. However, while the 10.7 kb construct induced ,markedly higher level with LPS than with dexamethasone, the 9.5 kb construct was less responsive to LPS, exhibiting a level of induction that was the same or reduced relative to that obtained with dexamethasone. Incultured primary hepatocytes from the AGP 10.7 line, the transgene was induced by IL-1, IL-6, or dexamethasone, administered individually or in combination. In contrast, the AGP transgene in hepatocytes from line AGP 9.5 responded only to dexamethasone, and was not affected by the peptide hormones. Together, these results provide strong support to the conclusions drawn from transfection experiments, and indicate that a minimum of two upstream sequences are responsible for the inflammatory induction of rat AGP. One element, located within the smaller 9.5 kb restriction fragment, is responsive to steroid hormones; it is likely that this element is the GRE located between positions −120 and −64. The other element, located between positions −5300 and −5150, is responsible for induction by inflammatory cytokines; this element is likely to be the DRE (Prowse, supra, 1988). Now that these lines are characterized with regard to their liver-specificity and inducibility by inflammatory stimuli, analysis of transgene expression in leukocytes and post-implantation decidual cells will be of interest to determine the relative roles of the DRE, GRE or other regulatory elements in the overall expression profile of rat AGP.

The transgenic lines will also be useful for studies of the function of AGP. For example, the response of cultured lymphocytes to a number of stimuli, including mitogens, sheep red cells, and allogeneic lymphocytes is inhibited by AGP, suggesting that the protein acts as an immunosuppressant. If AGP is, indeed, an immunosuppressant, then mice of line AGP 9.5-5, which accumulate some 20-fold higher levels of the protein in plasma relative to normal rats (Table 2), should exhibit reduced immune responsiveness.

More particularly, the animals of the invention can be used in the development of individual drugs to determine whether AGP influences their rate of clearance from the serum and their disposition among the tissues, as follows. Drug will be administered to the AGP transgenic lines that contain the supranormal levels of the compound and to control animals with normal levels of AGP. If AGP is influential then the rate at which the drug disappears from the blood will be different in the two groups. The amount of influence can be quantitated by comparing the results from the transgenic lines that contain different levels of transgene AGP. Furthermore measurement of drugs in various tissues at varioius times after drug administration to the different mice will allow an assessment of whether AGP affects the tissue distribution of the drug.

The animals of the invention also can be used to determine whether AGP levels are important modulators of drug action, as follows. Drug will be administered to the AGP transgenic lines that contain elevated levels of AGP and to control animals with normal levels of AGP. Depending on the pharmacological effect of the drug, physiological determinations will be performed on the two groups of animals at various times after drug administration to measure the physiological affect of the drug and whether the two groups of animals respond differently. Similar tests will be performed with different drug doses.

The animals of the invention can be used to test hypotheses of AGP function. Physiological processes considered to be modulated by AGP will be monitored in the transgenic mice and in control animals. Failure to observe a difference would indicate the likely non-involvement of AGP in that process.

Animals of the invention can be used to study the relative roles of the DRE and GRE in the expression of AGP in placenta and lymphocytes and in the induction of AGP by various disease states that include cancer, myocardial infarction, and arthritis.

Known techniques can be utilized to make such determinations.

We claim:

1. Transgenic mouse or the progeny thereof whose somatic and germline cells contain a stably integrated DNA sequence selected from the 9.5 kilobase NdeI and 10.7 kilobase EcoRI fragments spanning the rat AGP gene which is expressed in the mouse to produce rat alpha-1-acid glycoprotein, wherein levels of rat alpha-1-acid glycoprotein are increased in response to induction by an effective amount of a mediator of inflammation compared to uninduced levels.

2. A transgenic mouse or the progeny thereof according to claim 1 wherein said rat alpha-1-acid glycoprotein in the mouse is present in serum at a level of greater than 0.26 mg/ml under uninduced conditions.

* * * * *

UNITED STATES PATENT AND TRADEMARK OFFICE
Certificate

Patent No. 5,648,597                                                                             Patented: July 15, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Michael J. Dewey, Columbia, South Carolina; Heinz Baumann, Buffalo, New York; and Franklin G. Berger, Columbia, South Carolina.

Signed and Sealed this Nineteenth Day of May, 1998.

Jasemine C. Chambers, *SPE*
                                                                                                                        Art Unit 1632